Dec. 20, 1955 I. ISAKSON Plant Pat. 1,438
AVOCADO TREE
Filed Feb. 2, 1953.
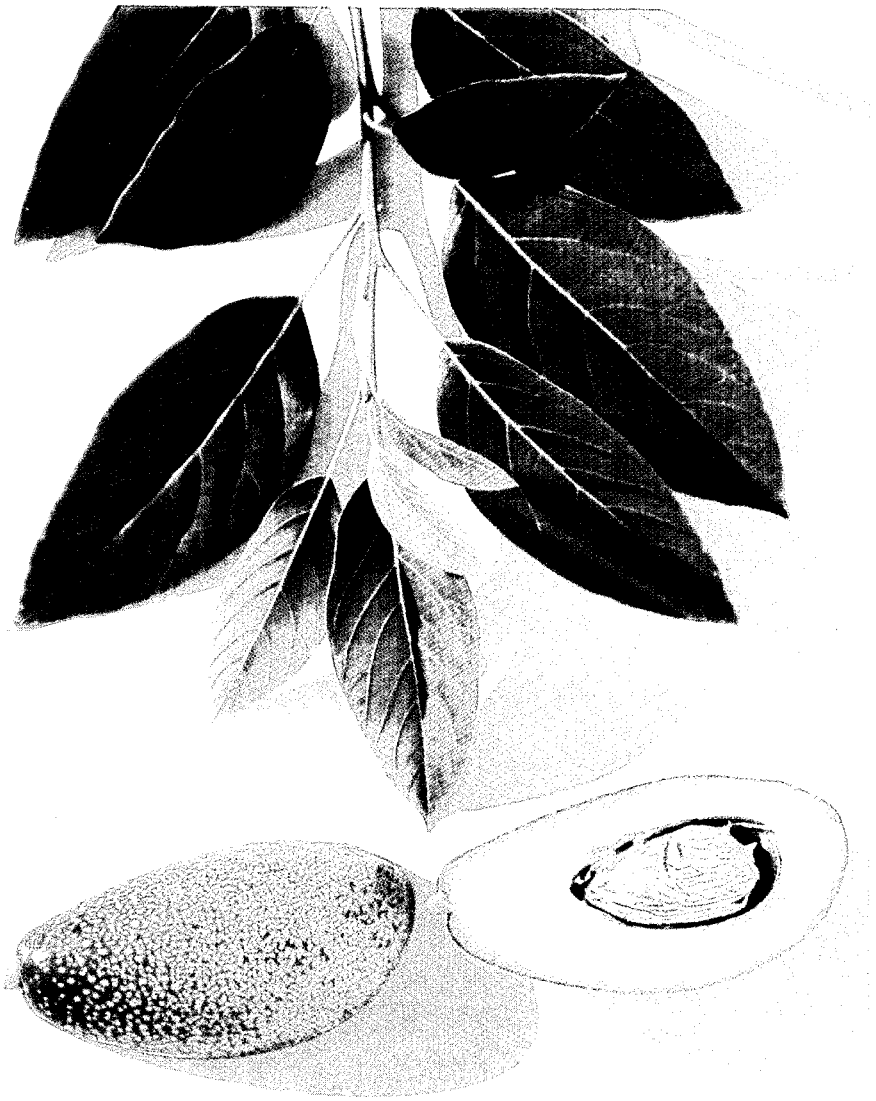
INGEGERD ISAKSON,
INVENTOR.
By C. A. Weidenhof
ATTORNEY.

United States Patent Office

Plant Pat. 1,438
Patented Dec. 20, 1955

1,438

AVOCADO TREE

Ingegerd Isakson, Arcadia, Calif., assignor, by direct and mesne assignments, of fifty-one per cent to Arthur S. Kimball, Monrovia, Calif., and forty-nine per cent to Weldon C. Wilkins, El Monte, Calif.

Application February 2, 1953, Serial No. 334,771

1 Claim. (Cl. 47—62)

This invention relates to a new and distinct variety of avocado tree. The avocado tree of this invention is characterized by its resistance to frost, such resistance being readily observable on trees grown on the foothill and inland valley areas of Southern California at distances of from thirty to fifty miles from the Pacific Ocean, where temperatures occasionally drop to 24°–27° F. for periods of time sufficient to completely defoliate most avocado trees and to cause branches up to one and one-half inches in diameter to die. During January 1 to January 6, 1949, the area around Duarte, California (where the new variety was raised and propagated by applicant), was subjected to a prolonged cold spell with temperatures dropping to 10° F. on three or four successive nights. The area immediately around the tree of this invention experienced temperatures of 23° F. to 25° F. for four successive nights in what was termed a "layer freeze" with lowest temperatures near the ground. Trees adjacent the tree of this invention were Haas (expired Plant Patent No. 139) and unpatented varieties known as Pueblo, Fuerte and Nabal, of substantially equal age. The Nabal was frozen down to the trunk. All of the other adjacent trees were defoliated and the Haas had to be radically trimmed, while no trimming was necessary on the tree of this invention. In addition to its remarkable resistance to frost, the new tree is characterized by a vigorous, regular habit of growth and bears green, thin-skinned, obloid fruit of good flavor and marketable size, the fruit reaching maturity during the months of October to December when raised in the central and eastern portions of Los Angeles County, California, for example, in the vicinity of Duarte.

The terminal foliage, as well as the fruit, of the new variety of avocado tree is illustrated in the appended color photograph.

It is believed that the tree of my new variety originated as a Mexican seedling (unpatented) and was one of a number of avocado seedlings planted, raised and propagated by applicant on applicant's property located in Duarte, Los Angeles County, California. Since destructive frosts are not an annual occurrence, the remarkable frost resistance of the tree was not apparent for some years. The tree began bearing fruit in a normal manner and after it withstood a killing frost, it was propagated and it was found that the frost-resisting characteristics, as well as the bearing characteristics, of the tree were retained.

As shown in the appended color photograph, the leaves are simple, elongated, emanate from well spaced and evenly distributed nodes and bifacient. The leaves appear to emanate from nodes at about 120° from each other. The leaves are broader for their length than those of the Gano (Patent No. 11) and are more open and flat. In general, the ratio of width to length of the leaves varies between about 1:1.8 to 1:2.3. The edges of the leaves are not excessively undulant, but instead, only slightly so, and exhibit a tendency to become slightly convex longitudinally. The foliage is well distributed and adequately protects the branches and fruit from sunburn. Young branches carry irregularly spaced, sap green lenticels which are not macroscopically prominent.

Young foliage varies in coloration from Pyrite Yellow or Sulphine to Olive Yellow (Ridgway, Color Standards, plates IV and XXX). Mature leaves range from Empire Green to Elm Green (plates XXXII and XVII). The veining on the face of the leaf is distinct and generally of a Yellowish Oil Green (plate V). Mature leaves are glossy and the underside is dull. In general, the color of the leaves is lighter in tone than those of the Fuerte or Ryan (both unpatented).

The fruit is obloid in form and not of the spheroid or pyriform shape. The fruit is provided with a thin skin which does not readily peel from the flesh. The background coloration of the skin of the fruit varies from Cress Green, Dark Cress Green, to Elm Green (plates XXXI and XVII). Stomata occur in elevated areas of the skin surface and are in greatest profusion at the base of the fruit opposite the stem. The stomata varies in coloration from Bright Chalcedony Yellow to Apple Green (plate XVII).

The fruit varies in size from about five ounces to nine ounces in weight, the average or mean being about six ounces. The fruit has good keeping qualities and a flavor normally graded as good plus, with negligible fibre and an oil content of between 16% and 19% for November and December fruit. The seed itself is somewhat pointed and provided with a seed coat which is thin to medium in thickness. The seed coat may, in many instances, adhere to the flesh and the entire seed may become loose when the fruit is left on the tree for a prolonged period. The meat or flesh of the fruit varies from Pale Chalcedony Yellow or Sulphur Yellow (plates XVII and V) to Seafoam Green (plate XXXI).

This new variety of avocado appears to be very readily propagated on Topa Topa or Ganter, both unpatented, root stock and the resulting trees are deemed to be of the Mexican variety in general characteristics. The tree of the present invention was propagated and reproduced by grafting on applicant's property in Duarte, California, and later at the Riverside Experimental Station at Riverside, California. It was also propagated by budding at Brea in Orange County and Puente, Los Angeles County, California.

The branching habit of the tree, although somewhat spreading, is distinctly different from the Fuerte; it does not crawl or spread like the Fuerte but instead, tends to branch in a generally upward direction, resulting in trees whose height is substantially equal to or only slightly greater than the width. This habit of growth reduces possibility of branch breakage under weight of fruit or winds.

I claim:

A new and distinct variety of avocado tree substantially as disclosed, characterized by distinctive resistance to frost and the ability to bear obloid, green, thin-skinned fruit during the late fall.

No references cited.